United States Patent [19]

Elsner

[11] Plant 5,059

[45] Jun. 7, 1983

[54] DISTINCT VARIETY OF GERANIUM NAMED GLACIER CARMEN

[75] Inventor: Wilhelm Elsner, Dresden, German Democratic Rep.

[73] Assignee: Oglevee Associates, Inc., Connellsville, Pa.

[21] Appl. No.: 320,001

[22] Filed: Nov. 10, 1981

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new geranium cultivar is distinguished by its brilliant color, short and compact plant, more basil branching, close internodes, small leaves and short flower stems with the flowers positioned immediately atop the foliage.

1 Drawing Figure

BACKGROUND OF THE NEW PLANT

The present invention comprises a new and distinct cultivar of *Pelargonium hortorum,* Bailey known by the varietal name of Glacier Carmen, formerly known as Karminball. The new variety is a seedling resulting from the cross of the seed parent Adonis and the pollen parent Fritz Ander.

The new cultivar was discovered in the year 1977 in Dresden, German Democratic Republic; was first asexually reproduced by cuttings in Dresden, German Democratic Republic and has been repeatedly asexually reproduced by cuttings at Oglevee Floral Company in Connellsville, Pa. over a three year period. It has also been trialed and field tested at Northwestern Washington State Experimental Station in Mt. Vernon, Wash. It has been found to retain its distinctive characteristics through successive propagations.

The new cultivar, when grown in a greenhouse in Connellsville, Pa., using natural light and 62° F. night temperature and 70° F. day temperature, has a response time of six weeks from a well rooted cutting to a flowering plant in a four inch (10 cm.) pot.

DESCRIPTION OF THE DRAWING

The accompanying photographic drawing illustrates the new cultivar, the color being as nearly true as possible with color illustrations of this type.

DESCRIPTION OF THE NEW PLANT

The following detailed descriptions set forth the characteristics of the new cultivar. The data which defines these characteristics were collected from asexual reproductions carried out by the Oglevee Floral Company in Connellsville, Pa. The plant history was taken on six week plants, blossomed under natural light in a greenhouse and color readings were taken indoors under 100 foot candles of cool, white fluorescent light. Color references are primarily to the R.H.S. Colour Chart of The Royal Horticultural Society of London.

THE PLANT

Classification:

*Botanical.*—*Pelargonium hortorum,* Bailey.

*Commercial.*—Zonal geranium.

Form: Bush.

Height: 12 to 18 cms. (15 cms. avg.) as a 4 inch pot plant excluding bloom and 22 to 28 cms. (25 cms. avg.) as a 4 inch pot plant including bloom.

Growth: Short and compact plant with more basil branching, closer internodes and smaller leaves as compared with commonly grown zonal geraniums.

Strength: Very sturdy with a low susceptibility to wind and rain damage.

Foliage: The quantity of foliage is of below average abundance.

Leaves:

*Size.*—7.5 to 10 cms. across.

*Shape.*—Reniform with oblique base.

*Margin.*—Crenate.

*Texture.*—Leathery and pubescent.

*Color.*—Upper side Green Group 137A; under side Green Group 138B.

*Ribs and veins.*—Palmate.

Petioles: 8 to 10 cms.

Stem:

*Color.*—Yellow Green Group 144B.

*Internodes.*—Very short, on the order of 1 cm.

THE BUD

Shape: Umbel formed with approximately 50 florets.

Size: As bud develops to color shown, head size is 3 cms. in diameter and it opens into a head size of 10 cms. in diameter.

INFLORESCENCE

Blooming habit: Continuous throughout the year.

Size: About 10 cms. across.

Borne: Singly in an umbel form.

Florets:

*Form.*—Flat to slightly cupped; nonsymmetrical and irregular in shape.

*Petals.*—6 to 7 in number plus 5 to 6 petaloids; upper side Red Group 52A; under side Red Group 48C.

*Size.*—Fairly large, 4.5 to 5 cms. across.

*Texture and appearance.*—Firm and satiny.

Petaloids:

*Quantity.*—5 to 6 in number.

*Shape.*—Small and twisted.

*Color.*—Same as florets.

Pedicel:

*Length.*—1 to 2 cms.

Peduncle:
*Length.*—10 to 18 cms.
Persistance: Nonshattering flower.
Disease resistance: Average to slightly better to Botrytis.
Lasting quality: On the order of three weeks.

REPRODUCTIVE ORGANS

Stamens:
*Anthers.*—Approximately 6 arranged cylindrical and carried at a height shorter than the stigma.
*Filaments.*—Pure white to red at the tips; 0.6 cms. in length.
*Pollen.*—Yellow in color.
Pistils:
*Number.*—1.
*Length.*—1 cm.

*Stigma.*—6 to 7 arms reflex back; reddish in color.
*Style.*—White.
Ovaries: Green; 5 carpels.
Fruit: Nonfertile.

The new cultivar is characterized by its brilliant color and a short and compact plant. There is more basil branching and close internodes and small leaves as compared with the standard bush zonal geraniums produced in the United States. A short flower stem positions the flower immediately atop of the foliage into the plants and renders the plant very resistant to wind and rain damage.

I claim:

1. A new and distinct variety of geranium plant substantially as herein shown and described.

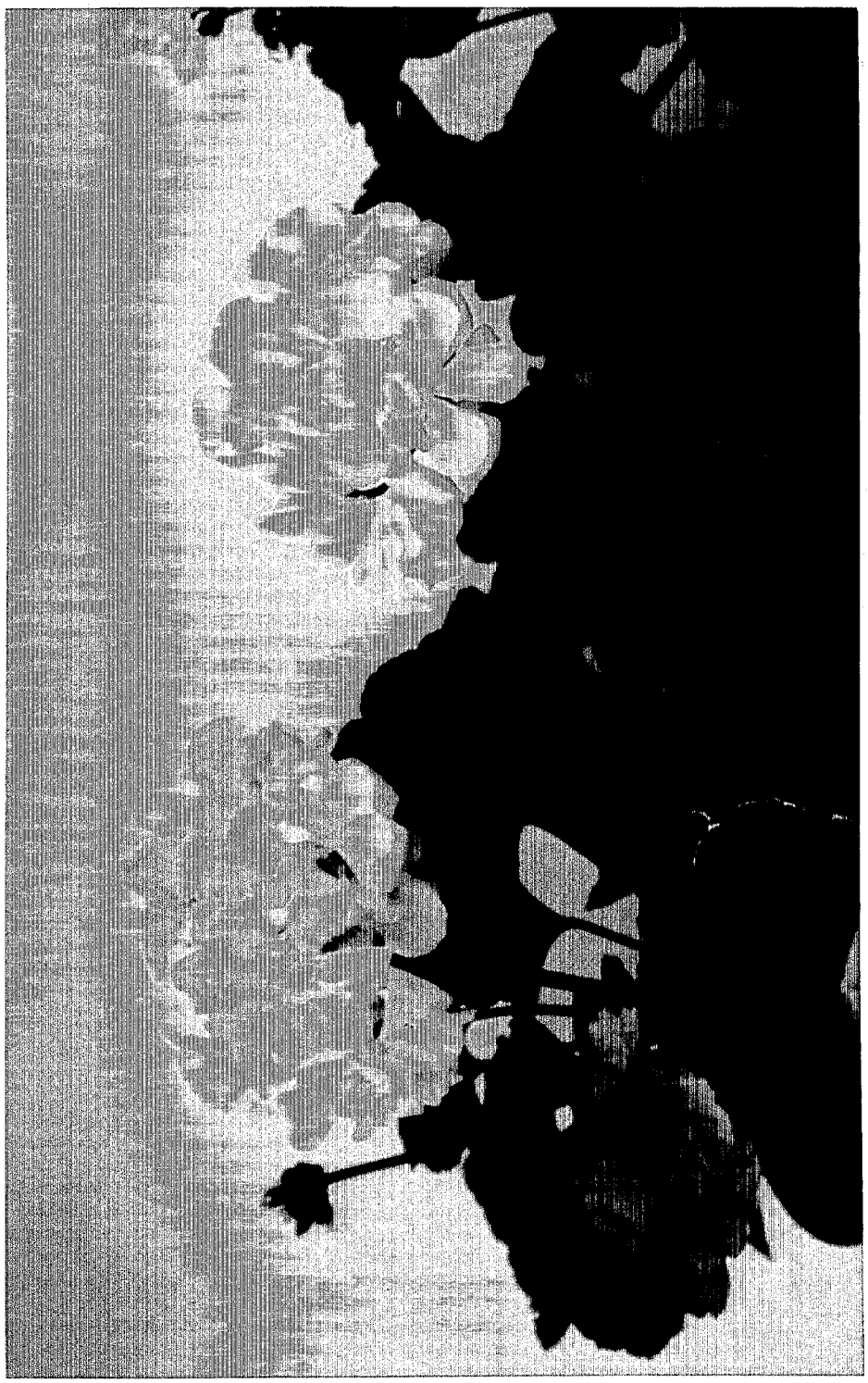

* * * * *